(12) United States Patent
Roitman et al.

(10) Patent No.: US 7,763,423 B2
(45) Date of Patent: Jul. 27, 2010

(54) SUBSTRATES HAVING LOW DENSITY REACTIVE GROUPS FOR MONITORING ENZYME ACTIVITY

(75) Inventors: Daniel Roitman, Menlo Park, CA (US); Paul Peluso, Hayward, CA (US); Mathieu Foquet, Redwood City, CA (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 927 days.

(21) Appl. No.: 11/240,662

(22) Filed: Sep. 30, 2005

(65) Prior Publication Data

US 2007/0077564 A1  Apr. 5, 2007

(51) Int. Cl.
| | |
|---|---|
| C12Q 1/68 | (2006.01) |
| C12Q 1/48 | (2006.01) |
| C12Q 1/34 | (2006.01) |
| C12N 11/14 | (2006.01) |
| C12N 11/02 | (2006.01) |
| C12N 11/08 | (2006.01) |
| C12N 11/06 | (2006.01) |

(52) U.S. Cl. .............. 435/6; 435/15; 435/18; 435/176; 435/177; 435/180; 435/181

(58) Field of Classification Search ............... None
See application file for complete search history.

(56) References Cited

U.S. PATENT DOCUMENTS

| | | | |
|---|---|---|---|
| 5,001,050 A | 3/1991 | Blanco et al. | |
| 5,198,543 A | 3/1993 | Blanco et al. | |
| 5,547,839 A | 8/1996 | Dower et al. | |
| 5,576,204 A | 11/1996 | Blanco et al. | |
| 5,624,711 A | 4/1997 | Sundberg et al. | |
| 5,723,584 A | 3/1998 | Schatz | |
| 5,821,058 A | 10/1998 | Smith et al. | |
| 5,874,239 A | 2/1999 | Schatz | |
| 5,919,523 A | 7/1999 | Sundberg et al. | |
| 5,932,433 A | 8/1999 | Schatz | |
| 6,028,025 A * | 2/2000 | Ying et al. ................. 502/171 |
| 6,210,896 B1 | 4/2001 | Chan | |
| 6,265,552 B1 | 7/2001 | Schatz | |
| 6,787,308 B2 | 9/2004 | Balasubramanian et al. | |
| 6,818,395 B1 | 11/2004 | Quake et al. | |
| 6,869,764 B2 | 3/2005 | Williams et al. | |
| 6,887,665 B2 * | 5/2005 | Trulson et al. ................. 506/16 |
| 6,917,726 B2 | 7/2005 | Levene et al. | |
| 6,982,146 B1 | 1/2006 | Schneider et al. | |
| 6,991,726 B2 | 1/2006 | Germain | |
| 7,013,054 B2 | 3/2006 | Levene et al. | |
| 7,033,762 B2 | 4/2006 | Nelson et al. | |
| 7,033,764 B2 | 4/2006 | Korlach et al. | |
| 7,052,847 B2 | 5/2006 | Korlach et al. | |
| 7,056,661 B2 | 6/2006 | Korlach et al. | |
| 7,056,676 B2 | 6/2006 | Korlach et al. | |
| 7,064,197 B1 | 6/2006 | Rabbani et al. | |
| 7,315,019 B2 * | 1/2008 | Turner et al. ................. 250/251 |
| 2002/0137053 A1 | 9/2002 | Ault-Riche et al. | |
| 2003/0186276 A1 | 10/2003 | Odera | |
| 2003/0190647 A1 | 10/2003 | Odera | |
| 2003/0194740 A1 | 10/2003 | Williams | |
| 2003/0215862 A1 | 11/2003 | Parce et al. | |
| 2004/0048301 A1 | 3/2004 | Sood et al. | |
| 2004/0224319 A1 | 11/2004 | Sood et al. | |
| 2005/0131219 A1 | 6/2005 | Urdea et al. | |

FOREIGN PATENT DOCUMENTS

| | | |
|---|---|---|
| EP | 1105529 B1 | 11/2005 |
| WO | WO 91/06678 | 5/1991 |
| WO | WO 96/27025 | 9/1996 |
| WO | WO 99/05315 | 2/1999 |
| WO | WO 00/36152 | 6/2000 |
| WO | WO 01/16375 A2 | 3/2001 |
| WO | WO 2004/055160 A2 | 7/2004 |
| WO | WO 2005/084367 A2 | 9/2005 |

OTHER PUBLICATIONS

M. J. Levene, et al., "Zero-Mode Waveguides for Single-Molecule Analysis at High Concentrations," *Science*, 299:682-686 (Jan. 31, 2003).

* cited by examiner

*Primary Examiner*—David M Naff
(74) *Attorney, Agent, or Firm*—Robert H. Reamey; Matthew B. Murphy

(57) ABSTRACT

Reactive surfaces, substrates and methods of producing and using such substrates and surfaces are provided. The substrates and surfaces provide low density reactive groups preferably on an otherwise non-reactive surface for use in different applications including single molecule analyses.

21 Claims, 7 Drawing Sheets

SUBSTRATES HAVING LOW DENSITY REACTIVE GROUPS FOR MONITORING ENZYME ACTIVITY

CROSS-REFERENCE TO RELATED APPLICATIONS

Not Applicable

STATEMENT REGARDING FEDERALLY SPONSORED RESEARCH

Not Applicable

BACKGROUND OF THE INVENTION

"God made the solid state. He left the surface to the Devil."
—Enrico Fermi

This sentiment is not new to materials scientists. The understanding, or lack thereof, as to the characteristics of a surface and its interactions with its environment has been at the center of monumental discoveries, and monumental failures. This issue permeates virtually every technological endeavor, whether it is in the field of engineering, chemistry or biology, whether it is focused on nanomaterials technology, extraterrestrial exploration, semiconductor technology, biotechnology manufacturing or pharmaceutical administration and delivery. While understanding the bulk properties of a material presents one problem, but the point at which that material ceases, and one must understand and/or deal with the properties of the surface of that material and how that surface will interact with its environment, is something altogether different.

The present invention is directed at materials and/or their surfaces that are selected and/or configured to meet a variety of different needs, including, inter alia, a capacity and ability of selective binding to desired molecules while preventing excessive binding of undesired molecules, and other advantageous characteristics that will be apparent upon reading the following disclosure.

SUMMARY OF THE INVENTION

The present invention is generally directed to substrates bearing modified surfaces that are useful in a variety of different, useful applications, as well as methods of producing such substrates and uses and applications of these substrates. In particular, the substrates of the invention possess surfaces with a selected density of reactive groups disposed on that surface, and preferably, a selected low density of such reactive groups.

In a first aspect, the present invention provides a substrate that comprises a surface comprising a first reactive moiety coupled thereto. In accordance with this aspect of the invention, the reactive moiety may be coupled to the surface at a density of between about 1 reactive moiety per 50,000 $nm^2$ and 1 reactive moiety per 100 $nm^2$. Similarly, the invention also provides an apparatus, comprising a surface having a reactive moiety coupled thereto, wherein the reactive moiety is coupled to the surface at a density of less than 1 reactive moiety per 100 $nm^2$.

Relatedly, the invention also provides devices that comprise a substrate having at least a first observation area provided therein, the observation area having an area of from about 100 $nm^2$ to 50000 $nm^2$. In accordance with these aspects of the invention, the substrates include from 1 to 3 reactive moieties coupled to the surface within the observation area.

The invention also provides methods of producing the susbstrates and devices of the invention by providing a substrate having a first reactive surface, and then providing a mixture of first and second surface modifying agents, wherein the first and second surface modifying agents are each capable of coupling to the reactive surface, and are present in the mixture at a first ratio selected so that the first and second surface modifying agents couple to the reactive surface at a second ratio. The reactive surface is then contacted with the mixture to produce the modified surface having first and second modifying agents coupled thereto at the second ratio.

Relatedly, also provided is a method of preparing a modified surface, comprising providing a surface to be modified, and contacting the surface to be modified with a surface modifying composition. In this aspect of the invention, the surface modifying composition comprises a first surface modifying agent coupled to a desired reactive moiety, and a second surface modifying agent not coupled to the desired reactive moiety. The first surface modifying agent and second surface modifying agent are present in the surface modifying composition at a ratio that produces the modified surface, wherein the reactive moieties are present on the modified surface at a density of between about 1 reactive moiety per 50,000 $nm^2$ and 1 reactive moiety per 100 $nm^2$.

In still another aspect, the present invention provides method of configuring a surface to provide a desired density of reactive moieties thereon, comprising treating the surface with a composition that substantially uniformly couples to the surface, the composition comprising a first component that does not contain the reactive moiety and a second component that comprises the reactive moiety, the second component being present in the composition at a concentration relative to the first component so as to provide the reactive moieties on the surface at the desired density.

DETAILED DESCRIPTION OF THE INVENTION

Figure 1:
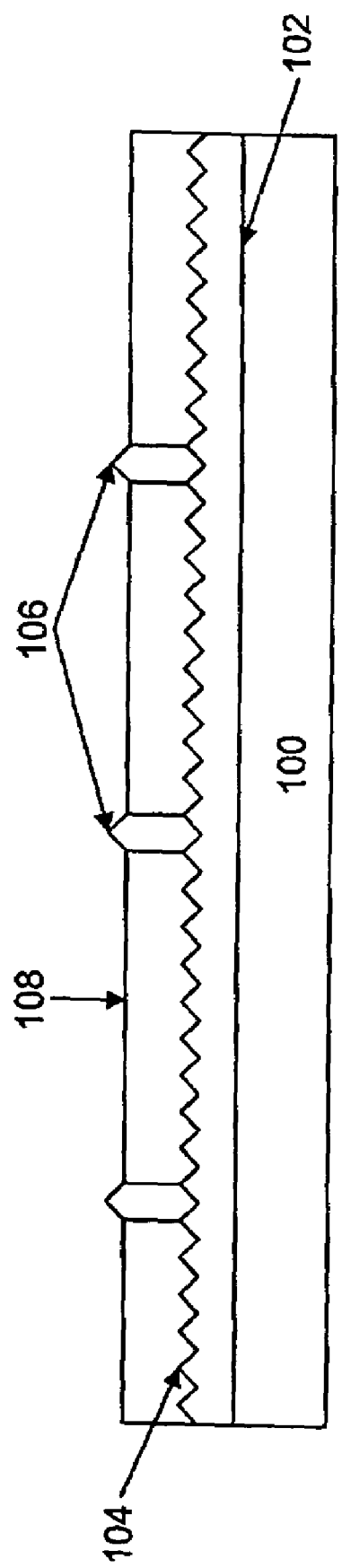
FIG. 1 is a schematic illustration of a surface having a low density of reactive groups thereon.

The present invention is generally directed to materials and their surfaces, generally referred to hereafter as substrates, where the surfaces have been selected and or configured to have desirable properties for a variety of applications. The invention is also directed to methods and processes for producing such surfaces, as well as methods and processes for using such surfaces in a number of different applications.

Of particular interest with respect to the present invention are substrates and surfaces that possess selective molecular binding or coupling characteristics, e.g., through the selective inclusion of molecular binding moieties thereon, and the use of such surfaces to selectively bind desired molecules to the surfaces in a selective fashion. Of still greater interest is the use of such surfaces when they are selectively coupled to chemically and/or biologically active molecules for use in chemical and/or biochemical processes, such as in preparative operations and/or analytical operations.

Although the invention has broad applicability, as will be apparent from the ensuing disclosure, in one particularly preferred example, surfaces having low density reactive groups include a single reactive group, in preferred cases, an enzyme, such as a nucleic acid polymerase, within an area that is being observed and/or monitored, giving the observer a real-time understanding of the reactions catalyzed by that single enzyme, e.g., DNA synthesis. Such systems are particularly useful in template dependent analysis, or sequencing, of nucleic acids.

I. Substrates and Surfaces

A. Generally

As alluded to above, the ability and/or propensity of surfaces to interact on a molecular level with their surroundings is of particular interest in the chemical and biological sciences and industries exploiting those sciences. For example, past efforts at manipulation of the reactive groups present on surfaces have focused primarily on one extreme or another. In particular, a number of applications benefit from maximizing the density of molecules bound to a particular surface by maximizing the number of reactive groups on that surface, e.g., high density binding. In other applications, the desired goal has been to exclude virtually all binding or other coupling interactions, including adsorbtion, between a surface and materials exposed to those surfaces, to create an inert surface for the given application, by capping or otherwise masking reactive groups on the surface.

In the case of biologically reactive surfaces for example, DNA array technology, for example, has focused upon binding as many active polynucleotide probes within a given area, so as to maximize the signal generated from hybridization reactions with such probes. Likewise, affinity surfaces employing, e.g., antibodies, have similarly focused upon increasing the density of binding groups on a surface to improve sensitivity. Alternatively, in a number of other applications, past efforts have been directed at effectively neutralizing the binding effects of surfaces to minimize or eliminate the surface's interaction with the chemical or biochemical environment. For example, the field of microfluidics, and particularly including the capillary electrophoresis art, is replete with examples of researchers identifying coating materials or other surface treatments that are intended to mask any functional groups of fused silica capillaries to avoid any molecular associations with those surfaces.

The present invention, however is directed at surfaces that are neither intended to maximize nor completely eliminate reactive chemical groups on a given surface. Instead, the present invention is directed at providing a surface with a selected relatively low density of reactive groups on a surface, and the use of such surfaces in a number of valuable applications. As will be appreciated, the nature of reactive groups does not imply or require a group capable of covalent linkage with another group, but includes groups that give rise to other forms of interaction, including hydrophobic/hydrophilic interactions, Van der Waals interactions, and the like. As such, surface reactivity, as generally described herein, includes, inter alia, association by covalent attachment and non-covalent attachment, e.g., adsorption.

Although, for ease of discussion, the substrates and surfaces are generally described herein in terms of planar solid substrates, it will be appreciated that the methods, processes, surfaces, etc. of the invention are applicable to a variety of different substrate types where the properties of reactive surfaces of the invention may be useful. In particular, such surfaces may comprise planar solid surfaces, including inorganic materials such as silica based substrates (i.e., glass, quartz, fused silica, silicon, or the like), other semiconductor materials (i.e., Group III-V Group II-VI or Group IV semiconductors), as well as organic materials such as polymer materials (i.e., polymethylmethacrylate, polyethylene, polypropylene, polystyrene, cellulose, agarose, or any of a variety of organic substrate materials conventionally used as supports for reactive media). In addition to the variety of materials useful as substrates, it will be appreciated that such materials may be provided in a variety of physical configurations, such as microparticles, i.e., beads, nanoparticles, i.e., nanocrystals, fibers, microfibers, nanofibers, nanowires, nanotubes, mats, planar sheets, planar wafers or slides, multiwell plates, optical slides including additional structures, capillaries, microfluidic channels, and the like.

In operation, this selective and limited reactivity of the surfaces of the invention is aimed at providing, in a limited fashion, a particular desired molecule or type of molecule of interest, typically a selected reactive molecule of interest, on a surface, e.g., a particular enzyme, nucleic acid, or the like, while preventing binding of the molecule of interest and/or other potentially interfering molecules elsewhere on the surface. For preferred applications, the desired result is a surface that includes a relatively low density of the selected reactive molecule surrounded by an otherwise non-reactive surface. Although discussed in terms of a molecule or type of molecule of interest, it will be appreciated that mixed functionality surfaces are also encompassed within the scope of the invention, including, e.g., two, three, four, or more different molecules or types of molecules of interest.

Thus, as used herein, the terms "reactive" and "non-reactive" when referring to different groups on the substrate surfaces of the invention refers to (1) the relative reactivity or association of such surface components with a given molecule of interest, and preferably also refers to (2) the relative reactivity or association of such surface components with other reagents in a given application of such surfaces, where such reagents may interfere with such applications, such as labeled reactants and or products that might interfere with detection, as well as inhibitors or other agents that would interfere with the progress of a reaction of interest at the reactive portion of the surface or elsewhere.

In terms of the first aspect of such reactivity, the reactive portions or groups on the surfaces will typically have 10 times greater affinity for the molecule of interest, preferably more than 100 times greater affinity and more preferably at least 1000 times greater affinity for the molecule of interest than the non-reactive surface. As such, it will be appreciated that the level of association between the molecule of interest and the reactive surface will be substantially greater than with the non-reactive surface under uniform conditions, e.g., more than 10 times greater, more than 100 times greater and preferably more than 1000 times greater. Such greater association includes greater frequency and/or greater duration of individual associations.

In terms of the second aspect of surface reactivity or non-reactivity, in many cases, such reactivity is coincident with the first aspect. In particular, where an enzyme constitutes the reactive portion of the surface, it will generally have a high affinity for its substrate, and thus associate with such substrate at a much greater level than the non-reactive portion, e.g., as described above. However, in some cases, the "reactive" portion of the surface may not include an ability to associate with certain potential interfering molecules. In such cases, the terms adsorptive and non-adsorptive also may be used. Nonetheless, it is desirable to prevent such interfering molecules from associating with the remainder of the surface. As such, the non-reactive surface may be defined in terms of its reactivity with such interfering components.

Because the primary source of undesirable interference for many applications lies in the non-specific interaction of reagents with the non-reactive portions of the surface, rather than at the desired reactive portion, the non-reactive surface in such cases, may generally be characterized by an association equilibrium constant between the non-reactive group and a particular interfering molecule that is preferably 10 fold lower than the association equilibrium constant of the reactive surface(s) with the reactive molecule(s), and preferably 100 fold (or more) lower. The association reaction for the non-reactive surface is also characterized by a low activation barrier, such that the kinetics of the corresponding dissociation reaction are expected to be fast, with average binding time preferably at least 10 fold lower than the significant timescales of the measurement process of the application, and preferably 100 fold lower or more.

As will be appreciated, the characteristics of such non-reactive and reactive surfaces will typically depend upon the specific application to which the surface is to be put, including environmental characteristics, e.g., pH, salt concentration, and the like. In particularly preferred aspects, environmental conditions will typically include those of biochemical systems, e.g., pH between about 2 and about 9, and salt levels at biochemically relevant ionic strength, e.g., between about 0 mM and 100 mM.

FIG. 1 provides a simplified schematic illustration of the surfaces of the invention, in block diagram form. As shown, a substrate 100 includes a surface 102. As noted elsewhere herein, the surface 102 is optionally derivatized to provide an overall active surface 104. As noted below, optionally, the substrate may inherently possess an overall reactive surface. The reactive surface 104 is then treated to provide a surface that includes reactive groups 106 coupled to the reactive surface 104 at relatively low densities. As noted below, these reactive moieties are preferably disposed upon or among an otherwise neutral or non-reactive surface 108. In particularly preferred aspects, the reactive groups 106 may include, or be further treated to include additional reactive groups, e.g., catalytic components, such as enzymes 110, or the like, as also shown in FIG. 1.

One important advantage of the surfaces of the invention is the provision of relatively isolated reactive groups. Isolation of reactive groups provides the ability to perform and/or monitor a particular reactivity without interference from adjacent reactive groups. This is of particular value in performing single molecule reaction based analyses, where detection resolution necessitates the isolation, e.g., to be able to optically distinguish between reactive molecules (optical isolation), electrochemically distinguish between reactions at different reactive molecules (electrochemical isolation) or where chemical contamination from one reaction at one location may impact reaction at an adjacent location (chemical isolation).

An additional advantage of the surfaces of the invention, is the ability of the remainder of the surface to be inert to coupling with potentially interfering molecules, e.g., fluorescent analytes or products. In particular, while binding of a few selected molecules is desirable for a set of applications, uncontrolled or nonspecific binding the remainder of the surface is often highly undesirable. By providing the desired reactive groups only at a selected, relatively low density, which themselves comprise a moiety having a desired reactivity, or which in some cases, are reacted with another molecule having the desired reactivity, one can selectively treat the remainder of the surface as necessary to render it effectively neutral to unwanted binding, thus substantially reducing or eliminating such unwanted binding elsewhere on the surface. In accordance with preferred aspects of the invention, both the provision of selected reactive groups and the provision of non-reactive groups over the remainder of the surface to reduce such unwanted surface interactions, are accomplished in the same process step or steps.

B. Density

In accordance with the invention, the low density of the selected desired reactive moieties or chemical groups on a surface is designed to provide a single reactive moiety within a relatively large area for use in certain applications, e.g., single molecule analyses, while the remainder of the area is substantially non-reactive. Typically, this means that any reactive groups otherwise present upon the remainder of the surface area in question are capped, masked, or otherwise rendered non-reactive. As such, low density reactive groups are typically present on a substrate surface at a density of reactive groups of greater than $1/1 \times 10^6$ nm$^2$ of surface area, but less than about 1/100 nm$^2$. In more preferred aspects, the density of reactive groups on the surface will be greater than 1/100,000 nm$^2$, 1/50,000 nm$^2$, 1/20,000 nm$^2$ and 1/10,000 nm$^2$, and will be less than about 1/100 nm$^2$, 1/1000 nm$^2$, and 1/10,000 nm$^2$. For certain preferred applications, the density will often fall between about 1/2500 nm$^2$ and about 1/300 nm$^2$, and in some cases up to about 1/150 nm$^2$.

C. Observation Areas

In particularly preferred aspects, the invention provides reactive groups on a surface at a density such that one, two, three or a few reactive groups are present within an area that is subject to monitoring or observation (an "observation area"). By providing individual or few reactive groups within an observation area, one can specifically monitor reactions with or catalyzed by the specific individual reactive group. Such observation areas may be determined by the detection system that is doing the monitoring, e.g., a laser spot size directed upon a substrate surface to interrogate reactions, e.g., that produce, consume or bind to fluorescent, fluorogenic, luminescent, chromogenic or chromophoric reactants, or fiber tip area of an optical fiber for optical monitoring systems, a gate region of a chemical field effect transistor (ChemFET) sensor, or the like, or they may be separately defined, e.g., through the use of structural or optical confinements that further define and delineate an observation area.

One example of a particularly preferred observation area includes an optical confinement, such as a zero mode waveguide (ZMW). Zero mode waveguides, as well as their use in single molecule analyses, are described in substantial detail in U.S. Pat. No. 6,917,726, which is incorporated herein by reference in its entirety for all purposes. Such ZMWs have been exploited for use in single molecule analyses, because they can provide observation volumes that are extremely small, e.g., on the order of zeptoliters. In such cases, the observation area will generally include the cross sectional area of the observation volume, and particularly that portion of the observation volume that intersects the surface in question.

In preferred aspects, the invention provides one or only a few reactive groups on the bottom surface of the waveguide. In such cases, the density is measured by the number of reactive groups divided by the surface area of the bottom surface of the waveguide. Thus, purely for purposes of exemplification, where a circular waveguide has a radius of 10 nm, and includes a single reactive molecule immobilized on its bottom surface, the density of reactive groups would be approximately $1/314$ nm$^2$. Thus, in terms of zero mode waveguides or other observation areas, and for purposes of example, it will be appreciated that reactive molecules present at a density of one, two, three or up to 10 reactive molecules in an area having a radius of between about 10 and about 100 nm, or areas from 314 nm$^2$ to about 31,416 nm$^2$, respectively (i.e., larger numbers of molecules in larger areas), are encompassed by the densities herein described. In preferred aspects, one, two or three molecules per observation area is generally preferred.

In many cases, ZMWs are provided in arrays of 10, 100, 1000, 10,000 or more waveguides. As such, immobilization of a single reactive group, e.g., an enzyme, within each and every ZMW would be difficult. However, dilution based protocols, when combined with the surfaces of the invention while producing some ZMWs that are not occupied by an enzyme, will generally result in the majority of occupied ZMWs (those having at least one enzyme molecule immobilized therein) having only one or the otherwise desired number, of enzymes located therein. In particular, in the case of ZMWs having reactive molecules like enzymes located therein, typically, more than 50% of the occupied ZMWs will have a single or the desired number of reactive molecules located therein, e.g., a particular type of enzyme molecule, preferably, greater than 75%, and more preferably greater than about 90% and even greater than 95% of the occupied ZMWs will have the desired number of reactive molecules located therein, which in particularly preferred aspects may be one, two, three or up to ten reactive molecules of a given type. As noted elsewhere, in some circumstances different reactive molecules may also be provided at a desired density to provide a mixed functionality surface. In accordance with the present invention, depending upon the types of reactive groups being referenced, e.g., catalytic or binding, it will be appreciated that the determination of density may be applied on a single occupied ZMW, or upon multiple ZMWs in an array.

D. Specific Reactive Groups

The reactive groups or moieties present on the surfaces of the invention include a wide range of different types of reactive groups having chemical and/or biological activity, which are coupled to a surface of a material or substrate, either by exogenous addition or which inherently are present on such surface. These reactive groups include groups on a surface that possess binding activity for other chemical groups, e.g., the ability to bind another chemical moiety through specific or non-specific interactions, through covalent attachment, Van der Waals forces, hydrophobic interaction, or the like. Provision of a wide range of reactive groups on surfaces is readily understood in the art, and includes, for example, ionic functional groups, polyionic groups, epoxides, amides, thiols, hydrophobic groups, e.g., aliphatic groups, mono or polycyclic groups, and the like, e.g., as generally used in reverse phase and/or hydrophobic interaction chromatography (HIC), staudinger ligation groups (see, e.g., Lin et al., J. Am. Chem. Soc. (2005), 127:2686-95), Click chemistry coupling using chemoselective azide-acetylene linkages (See, Deveraj et al., JACS 2005, 127:8600-8601; Lummerstorfer et al., J. Phys. Chem. B (2004) 108:3963-3966, and Collman et al., Langmuir (2004) 20:1051-1053, each of which is incorporated herein by reference in its entirety for all purposes) and other groups that associate or are capable of being coupled with other groups in a non-specific fashion. Additionally, use of specific binding groups on surfaces, e.g., groups that specifically recognize a complementary binding partner has been described, including, e.g., complementary nucleic acid pairs, antibody-epitope pairs, binding peptides that recognize specific macromolecular structures, e.g., recognition sequences in proteins, peptides or nucleic acids, lectins, chelators, biotin-avidin linkages, and the like.

Identification of the number and/or density of reactive groups may generally be ascertained through the use of a reporter molecule, which in many cases, may be the reactive group itself. In particular, and by way of example, one can ascertain the number of enzyme molecules coupled to a surface area by assaying for the activity of that enzyme. Likewise, other reactive groups may be quantified through other methods, e.g., titration, coupling of labeling groups, or the like.

As used herein, both reactive groups and non-reactive groups envision an environment in which the surfaces are to be applied, and in which the reactivity, or non-reactivity is evident. As will be appreciated, different groups may be reactive in certain environments and non-reactive in others, and the invention, as broadly practiced, envisions applicability in a wide range of different environments. For ease of discussion, and in preferred aspects, the surfaces of the invention are most often to be applied in biological or biochemical reactions, and as such are subjected to appropriate environments. Such environments typically include aqueous systems having biochemically relevant ionic strength, that range in pH between about 2 and about 9, and preferably between about 5 and about 8, but may vary depending upon the reactions being carried out.

In certain preferred aspects, the reactive chemical groups also include groups having catalytic activity, e.g., the ability to interact with another moiety to alter that moiety other than through binding, i.e., enzymatic activity, catalytic charge transfer activity, or the like. In particularly preferred aspects, the active chemical groups of the invention include chemical binding groups, and optionally and additionally, catalytic groups, where the binding group is used to couple the catalytic group to a given surface in accordance with the invention. For example, an enzyme or other catalytic group may be coupled to a surface via an intermediate binding or linker group that is, in turn, coupled directly to a reactive group that is disposed upon the surface material at a desired density.

A number of different reactive groups may be employed in accordance with the invention, and may to some extent, depend upon the surface being used, and whether the reactive group is intended to provide a low-density general or non-specific binding or associative function, a low-density specific binding function, or a low density catalytic function.

For example, for silica based surfaces, e.g., glass, quartz, fused silica, silicon or the like, reactive groups may be provided by silane treatment of the surface, e.g., using epoxysilane, aminosilane, activated carboxylic acid silane, isocyanatosilane, aldehyde silane, mercaptosilane, vinyl silane, hydroxyterminated silanes, acrylate silane and the like. Such treatments may yield the reactive groups, e.g., in terms of low density, non-specific associative groups, or they may result in or be further treated, to provide a specific binding group or catalytic group, as the ultimate reactive group. Alternatively or additionally, other inorganic or organic reactive groups may be provided upon a surface. In the case of inorganic surfaces like silica based substrates, such additional materials may be coupled to the surface via an intermediate chemical coupling, e.g., using silane chemistry, i.e., as described above. These additional materials may include small molecules, e.g., ionic groups, metal ions, small organic groups, as well as larger or polymeric/oligomeric molecules, e.g., organic polymers. For ease of discussion, polymer and oligomer are used interchangeably herein to refer to molecules that include multiple subunits of similar chemical structure.

In particularly preferred aspects, a longer linker molecule, and preferably an organic linker molecule may be used to link the reactive group to the surface to provide further flexibility to the overall linkage, e.g., by providing greater spacing between the surface and reactive group. In particular, polymeric or oligomeric chains that bear the desired reactive group at one end, may be linked at the other end to the surface, e.g., via silane linkage in the case of a glass surface. By selecting different types and lengths of polymer linkers, one can further adjust the properties of the surface, e.g., relative hydrophobicity of different groups/areas, relative distance to the surface, overall or local surface charge, and the like. Examples of useful polymer linkers include, e.g., cellulosic polymers (such as hydroxyethyl-cellulose, hydroxypropyl-cellulose, etc.), alkane or akenyl linkers, polyalcohols (such as polyethyleneglycols (PEGs), polyvinylalcohols (PVA)), acrylic polymers (such as polyacrylamides, polyacrylates, and the like), polyethylene polymers (such as polyethyleneoxides), biopolymers (such as polyamino acids like polylysine, polyarginine, polyhistidine, etc.), other carbohydrate polymers (such as xanthan, alginate, dextrans), synthetic polyanions or polycations (such as polyacrylic acid, carboxyl terminated dendrimers, polyethyleneimine, etc.) and the like. Again, depending upon the type of linker used, the linker may further include a desired reactive group coupled to it.

While described generally in terms of application of a reactive group to the surface, it will be appreciated that the active group may be applied to the surface as an inactive or less reactive precursor to the desired reactive group, and subsequently activated to yield the desired reactive group. In particular, the reactive groups may be provided as photo, thermally or chemically activatable precursor groups, e.g., bearing a photolytic capping group, a temperature sensitive capping group or an acid or base labile capping group, blocking the reactive moiety of interest. The group may then be selectively activated, e.g., through the use of photo, thermal or chemical treatment to yield the desired surface. A variety of such groups are known in the art and are described in, e.g., Guillier, et al., Linkers and Cleavage Strategies in Solid Phase Organic Synthesis and Combinatorial Chemistry, Chem. Rev. 100:2091-2157 (2000).

As noted above, the reactive groups on a surface may be comprised of the aforementioned specific or non-specific binding moieties, or may include catalytic groups that are coupled to the surface, either directly to the surface, through the above mentioned specific or non specific binding or associative groups, that are, in turn, coupled directly or indirectly to the surface, or through additional specific or non-specific binding groups coupled to the surface. Catalytic groups may include catalytic chemicals, e.g., catalytic metals or metal containing compounds, such as nickel, zinc, titanium, titanium dioxide, platinum, gold, or the like. In preferred aspects, however, the catalytic groups present at a desired low density on the surfaces of the invention comprise bioactive molecules including, e.g., nucleic acids, nucleic acid analogs, biological binding compounds, e.g., peptides or proteins, biotin, avidin, streptavidin, etc., and enzymes. In the case of nucleic acids or nucleic acid analogs, such surfaces find use in a variety of specific binding assays, e.g., to interrogate mixtures of nucleic acids for a nucleic acid segment of interest (See, e.g., U.S. Pat. Nos. 5,153,854, 5,405,783, and 6,261,776). Likewise, binding proteins and peptides are often useful in interrogating biological samples for the presence or absence of a given molecule of interest. Typically such proteins or peptides are embodied in antibodies or their binding fragments or binding epitopes of such antibodies. In particularly preferred aspects, the surfaces of the invention bearing the catalytic groups comprise an enzyme of interest and are used to monitor the activity of that enzyme. A wide variety of enzymes are regularly monitored and detected in biological, biochemical and pharmaceutical research and diagnostics. Examples of preferred enzymes include those monitored in genetic analyses like DNA sequencing applications, such as polymerases, e.g., DNA and RNA polymerases, nucleases (endo and exonucleases), ligases, and those involved in a variety of other pharmaceutically and diagnostically relevant reactions, such as kinases, phosphatases, proteases, lipases, and the like.

With respect to immobilization of enzymes on surfaces in accordance with the invention, yet a further advantage of the surfaces of the invention stems from the combined advantages set forth elsewhere herein. In particular, in selectively immobilizing biomolecules, like enzymes, through specific linkages, and rejecting their adsorption elsewhere on the surface, the activity of the biomolecules present on the surface can be more selectively preserved, where mere adsorption may have yielded a significant population of inactive or less active molecules. Thus, the resulting surface, the biomolecules present, while present at low density, will nonetheless be present at a relatively high specific activity, e.g., number of active biomolecules of interest vs. total number of biomolecules present).

In the case of certain catalytic reactive groups, e.g., enzymes, the density of such reactive groups further envisions the density of active molecules, as opposed to immobilized inactive molecules. For example, in the case of enzymes immobilized on a surface at a relatively low density, such density will typically include an allocation for the specific activity of the immobilized enzyme, e.g., the efficacy of the immobilization process. Thus, where the immobilization process yields only 50% viable or active enzymes, the overall density of enzyme molecules active and otherwise, will generally be 2× the density of active molecules. Accordingly, in ascertaining the desired density of such reactive groups, it is often desirable to assess the relative efficacy of the immobilization process in depositing active molecules. As noted elsewhere herein, certain aspects of the methods of the invention are particularly useful at retaining very high specific activity of enzymes immobilized on the surfaces (See Examples), and preferably will provide specific activities (fraction of immobilized enzyme having activity) of greater than 20%, greater than 30%, more preferably, greater than 50% and in still more preferred aspects, greater than 75%, and in some cases greater than 90%.

In contrast to the low density of desired reactive groups on the substrates of the invention, it is also typically preferred that the remainder of the surfaces in question be non-reactive. As noted previously, such non-reactivity includes a substantially lower affinity for a molecule of interest as compared to the reactive groups, but additionally, preferably includes a lack of excessive binding or association with molecules that would potentially interfere with the end-application of the surface. For example, where additional catalytic groups are to be coupled to a desired low density population of desired reactive groups on a surface, it is generally desired that such catalytic groups not associate substantially with the remainder of the surface, either specifically or non-specifically. Likewise, where in applications, additional chemical groups will be exposed to the surfaces of the invention, it will generally be desired that the remainder or non-reactive surface not catalyze reactions with such materials or bind or otherwise associate with the materials that might provide adverse or noisy signals that do not correspond to the reactions of the reactive groups of interest.

In the case of fluorescent single molecule assays, one particular desire is to avoid excessive (e.g., in duration and/or frequency), nonspecific binding or association or "sticking" of unreacted fluorescent reagents or fluorescent products, with the surface other than with the reactive groups of interest, e.g., an enzyme, as such associations can lead to erroneous signal production, background signal noise and signal noise build-up over time. In general, it will be desired that non-specific association of compounds with the non-reactive portion of the surface will be comparable to the rate of diffusion of such compounds in solution. Rephrased in terms of labeled compounds being observed in observation areas or optical confinements, signal resulting from the non-specific association of compounds with the non-reactive surface will typically be on the same or similar order, e.g., less than 100 times such diffusion based signals and preferably less than 10 times such diffuson based signals (in either or both of duration and frequency), as signal resulting from random diffusion of such compounds into and out of the observation area or volume of fluid for a given analysis. In terms of fluorescent compounds or other signal generating compounds that might potentially interfere with the desired application, it will generally be desirable that any signal resulting from association of such compounds with the non-reactive surface (referred to herein as "non-specific signal generation"), will be at least 10 fold lower than signal generated by the reactive groups, preferably more than 100 fold less, and still more preferably, more than 1000 fold less than signal resulting from action of the reactive molecules ("specific signal generation"), e.g., desired enzyme activity. Such reductions in non-specific signal generation includes reductions in either or both of frequency or duration, e.g., reductions in the number of signal events or a reduction in the aggregate amount of signal emanating from such non-specific signal generation.

A variety of non-reactive groups may be employed upon the remainder of the surface that will, again, depend upon the environment to which the surface will be subjected. In general, however, terminal hydroxyl groups, methyl groups, ethyl groups, cyclic alkyl groups, methoxy groups, hydroxyl groups, e.g., in non-reactive alcohols and polyols, inactivated carboxylate groups, ethylene oxides, sulfolene groups, hydrophilic acrylamides, and the like.

E. Layered Surfaces/Thickness

As repeatedly described above, the reactive groups, as set forth above, may be coupled directly to the surfaces of the substrates or coupled through one or more intermediate linking groups that provide one or more intermediate molecular layers between the desired reactive group and the inherent or native surface of the substrate material. Restated, each component of the surface, reactive or non-reactive, may result from one or more layers of components to provide the desired resulting surface component.

For example, in its simplest form, both reactive and non-reactive groups may be coupled directly to a substrate's native surface to yield the low-density reactive surfaces of the invention. Alternatively, one or more layers of linking groups may be added to the surface to yield a layered surface, to which the reactive and non-reactive groups are then coupled to yield the desired surface. In either of these cases, the process for apportioning reactive and non-reactive groups on the surface occurs in the deposition of the final layer.

In still more complex configurations, apportionment of the reactive and non-reactive groups on the final surface layer may occur in the selection and deposition of earlier layers on the surface. In other words, a first low-density reactive layer may be used to dictate the deposition of a subsequent or desired low-density reactive layer. By way of example, a first layer that includes a low density of non-specific binding groups may be used as a template for the deposition of a subsequent layer with a low density of catalytic groups, e.g., where the catalytic groups couple to the binding groups. In still further aspects, such apportionment may take place over multiple layers, to more finely tune the deposition process. For example, a first apportioned layer, e.g., including a mixture of binding groups and nonbinding groups, may underlie an additional layer that includes a further apportionment. Such complex layers are also particularly useful in depositing surfaces according to the invention that include a number of different types of reactive groups on an otherwise non-reactive surface, e.g., different enzymes, different nucleic acids, different antibodies, and the like.

In accordance with the foregoing, in some cases, a surface's inherent properties may permit coupling of reactive or intermediate groups thereto, in many cases, the surfaces must first be derivatized to provide reactive groups, either for use as such, or for further coupling to intermediate linking groups. In many cases, the derivatization process may be concurrent with the coupling of reactive groups by providing the desired reactive group as a constituent of the derivatizing chemical. In such cases, the derivatizing agent bearing the reactive group of interest is coupled to the surface at a relatively low density. Typically, and as set forth in greater detail below, this is accomplished by providing the derivatizing agent bearing the reactive group of interest in an appropriate ratio with derivatizing agent that, other than its ability to modify the surface, is substantially non-reactive.

In alternative configurations, the entire surface may be derivatized using any of the aforementioned reactive groups to provide a reactive surface to which an intermediate linking group may be coupled. In such cases, the intermediate linking group, which is provided in a ratio of linking group bearing a reactive group of interest and a non-reactive linking group is then contacted with the reactive surface to provide the desired density of reactive groups of interest on the ultimate surface. As will be appreciated, an intermediate reactive or coupling group may be provided at a higher density than the density at which the desired, final reactive group is provided, depending upon the level of coupling of that final group to the intermediate group. For example, if it is anticipated (or even planned) that the final reactive group will couple to the intermediate coupling group at a rate of 1 linkage for every ten intermediate groups, then such intermediate reactive groups may be present at a level 10 times higher. Typically, when employing such intermediate reactive groups, their density will be between about 1 and about 1000 times greater than the final reactive group, often between about 1 and about 100 times, and in some cases from 1 to about 10 times greater than the density of the final reactive group, e.g., an enzyme.

Figure 2:
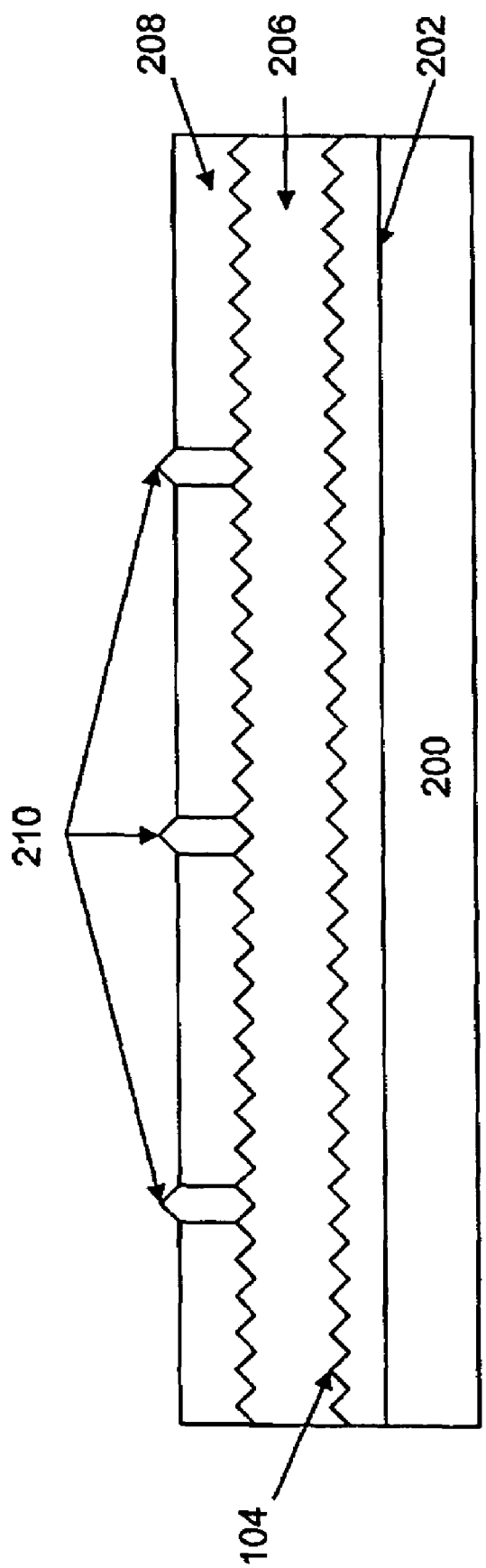
FIG. 2 is a schematic illustration of a substrate having a layered, or multitiered functionalization to provide a relatively low density of reactive groups thereon.

One example of such a "layered" surface is schematically illustrated in FIG. 2, which provides a substrate 200 having an initial or inherent surface 202 that is treated or derivatized to provide an overall reactive surface 204 to which additional chemicals may be coupled. Reactive surface 204 has coupled thereto a linker/spacer layer 206 which in turn bears the terminal layer 208. Terminal layer 208 includes at relatively low density, reactive groups 210 interspersed among the remainder of the terminal layer 208. The number, type, and order of layers may be varied in accordance with the various aspects of the invention described herein and to achieve the desired final surface.

II. Methods of Preparing Substrates and Surfaces

A number of methods may be used to prepare the surfaces of the invention. In at least a first approach, the methods of the invention that are used, apply a ratio or dilution based treatment to a surface to yield the desired density. In particular, a simple surface modification protocol would employ a mixture of at least two different surface modifying agents where the first agent included, in addition to the moieties for coupling to the surface, the reactive group of interest, such that coupling of the first agent to the surface would also provide the reactive group in a configuration that preserved its reactivity. The second or diluent agent would, other than its ability to couple to the surface be otherwise unreactive to the environment of the application to which the surface was to be put.

Figure 3:
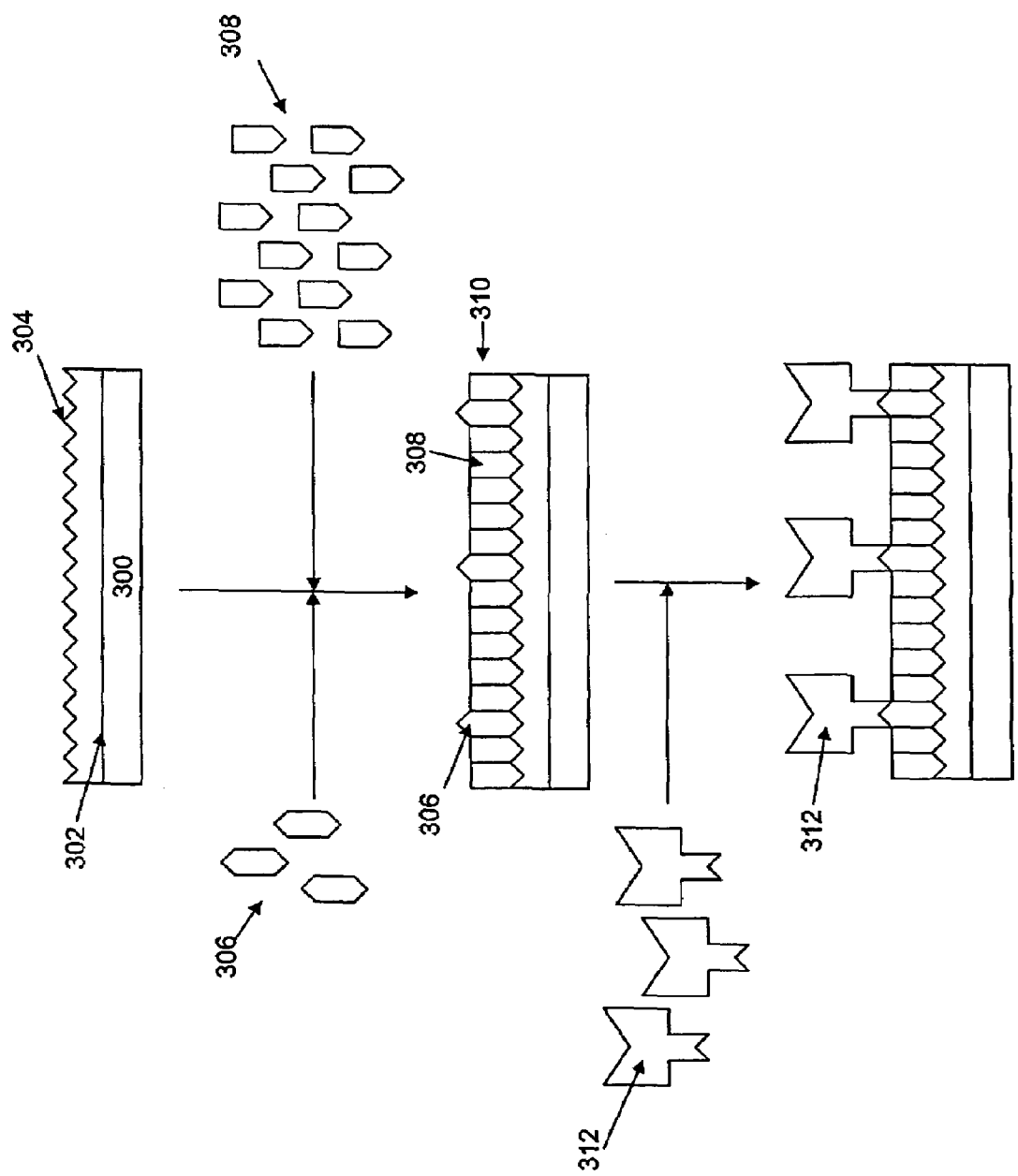
FIG. 3 schematically illustrates one exemplary process for producing the surfaces of the invention.

A schematic illustration of the process is illustrated in FIG. 3, similar to the diagram shown in FIGS. 1 and 2. As shown, a surface, i.e., glass or silica based surface 304 on substrate 302 is initially derivatized, e.g., using silane chemistry to provide an overall reactive surface 304. The reactive surface 304 is then treated with a mixture of surface modifying agents 306 and 308, that are capable of coupling to the reactive surface 304. The mixture of agents includes a concentration of agents bearing a reactive group of interest 306, and a concentration of agents that provide non-reactive groups 308. The two agents are present in a ratio that provides for binding of the agents to the reactive surface 304 at the desired density of reactive groups 306 on that surface. For example, where binding kinetics of coupling of both modifying agents to the reactive surface are equal, a 1:10 ratio of reactive agent 306 to non-reactive agent 308 would effectively yield a density ratio of 1 reactive group 306 coupled to the reactive surface 304 for every ten non-reactive groups 308 on that surface. Following contact and coupling to the reactive surface 304, a ultimate substrate surface 310 bears the desired reactive groups (provided by agents 306) at a desired relative density. For ease of discussion, the surface modifying agents and the groups that result on the surface from their use are illustrated using the same diagrammatical and numerical representations, although it will be appreciated that the agents and the resulting groups may have different chemical structures.

In a related, but alternative exemplary method, the initial derivatization process yields a substrate surface having low density reactivity, using a mixture of different surface derivatizing agents. For example, a silica based surface may be initially derivatized using a mixture of silane reagents including a first silane reagent that includes a reactive group when coupled to the surface, e.g., an aminosilane, with a silane reagent that is capped or otherwise nonreactive, e.g., a hydroxylsilane, methylsilane, fluoroalkylsilane, or the like. With reference to FIG. 3, for example, the initial derivatization process might employ a mixture of silanes that bear no additional reactive moiety, e.g., they are capped, blocked or otherwise non-reactive, and silanes that include the reactive group of interest. Derivatization with this mixture would produce substrate surface that included a low density reactive layer, e.g., similar to layer 310, in place of overall reactive layer 304.

As noted previously, in any of the cases described above, the reactive group of interest that is first coupled to the surface at a relatively low density, may be the ultimate desired reactive group for the desired end-application, or it may be an intermediate linking group that is capable of linking to the ultimate reactive group. By way of example, the low density reactive surface 310 shown in FIG. 3, may be further treated with the particular reactive group of interest, e.g., enzyme 312, to couple enzyme 312 to reactive groups 306. The enzyme may additionally be treated to render it more amenable to coupling to the reactive groups, e.g., through the incorporation of linker moieties, specific binding partners to reactive groups 306, or the like. By way of example, the reactive groups may include one member of a specific binding pair, e.g., avidin, while the enzyme 312 includes the complementary member of the binding pair, e.g., biotin. Coupling of the enzyme 312 (the ultimately desired reactive group) to the existing or intermediate reactive group 306 then involves contacting the enzyme with the surface under conditions conducive to the affinity interaction between the complementary binding pair members.

As will be appreciated, the methods of providing the low density reactive surface may be approached from a number of different directions, while still yielding similar results. For example, with reference to and as shown in FIG. 3, above, the surface modifying reactive groups 306 which are used to couple enzyme 312 to the substrate surface 302 are first diluted with surface modifying non-reactive groups 308, to yield a low density template to which the enzyme (or other reactive group of interest) is coupled.

Alternatively, a subset of surface modifying reactive groups 306 may be pre-coupled to the enzyme 312 and then diluted with reactive surface binding agents 306 (or optionally, non-reactive surface modifying agents 308) in an appropriate dilution to yield the desired density when coupled to the reactive surface 304.

Figure 4:
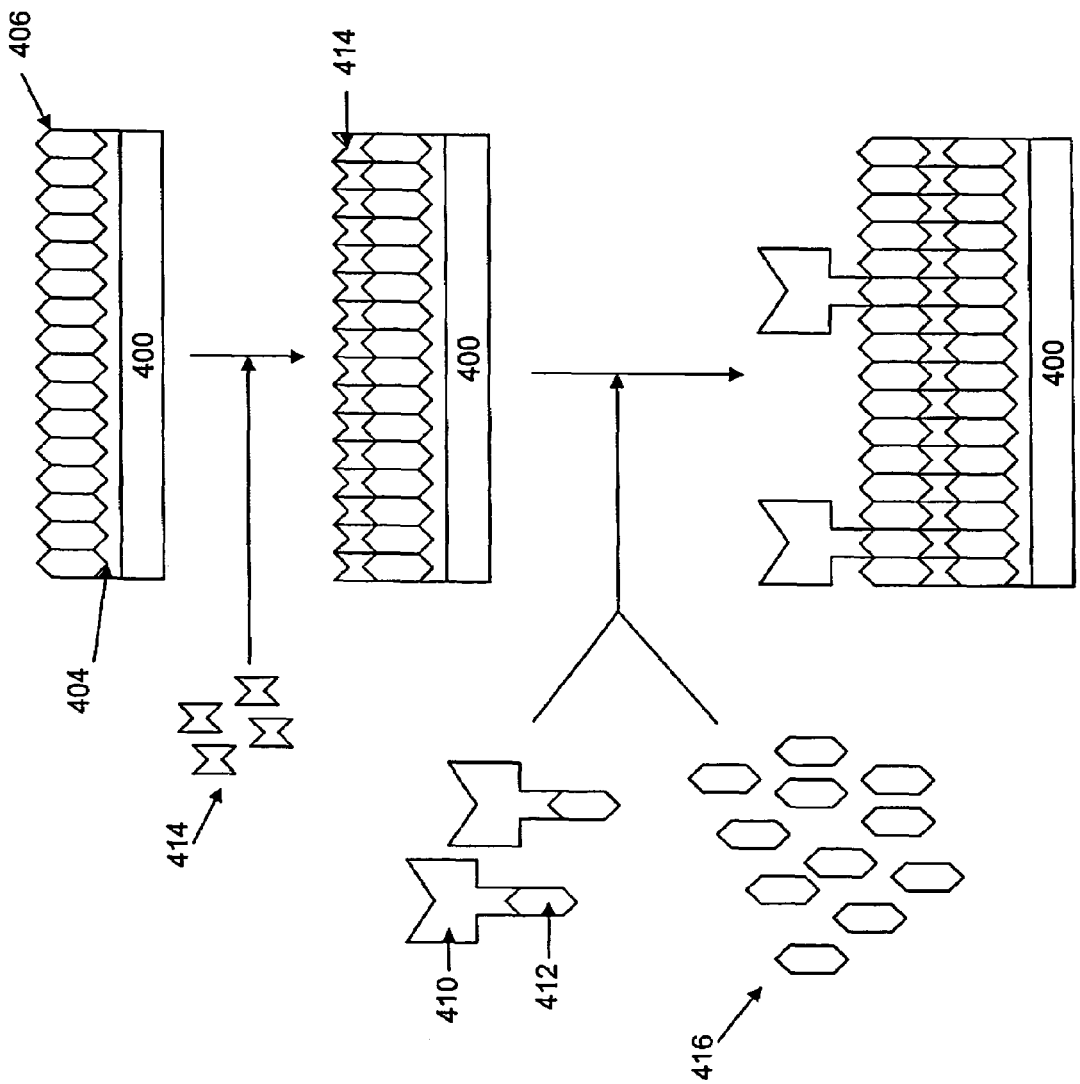
FIG. 4 schematically illustrates another exemplary process for producing the low density reactive surfaces of the invention.

An example of this process is schematically illustrated in FIG. 4. As shown, a substrate 400 having a derivatized surface 404 is substantially uniformly biotinylated to provide a substantially uniformly biotinylated surface 406. An enzyme 410, bearing a coupled biotin moiety 412 is then coupled to the biotinylated surface 406 using an intermediate avidin/streptavidin linkage 414 (hereafter referred to as avidin, for simplicity of description). In one aspect, the biotinylated surface 406 may be uniformly treated with avidin 414 to provide a uniform avidin surface. In order to then provide the enzyme 410 at a relatively low density, the biotinylated enzyme 410/412 is optionally mixed with biotin 416 that does not include the enzyme, at a ratio intended to yield the desired density of enzyme when the mixture is coupled to the overall biotinylated surface 406. Alternatively, instead of treating the biotinylated surface 406 with avidin 414, and applying a mixture of biotinylated enzyme 410/412 and free biotin 416, one could mix biotinylated enzyme 410/412 with an excess of avidin 414 at a desired ratio and apply it to biotinylated surface 406 to yield the same low density of enzyme coupled to biotinylated surface 406 via the avidin/biotin linkage. In this case, assuming purely for the sake of example that the rate of coupling to a biotinylated surface is equivalent for avidin coupled to a biotinylated enzyme and uncomplexed avidin, a mixture of such species at a ratio of 1:10 would yield approximately a density of enzyme to uncomplexed avidin on the surface of 1:10. As will be appreciated, this assumption is simplified for ease of example, and actual binding rates would likely vary significantly, but would generally be readily calibrated through routine experimentation.

Again, although described in terms of enzymes linked via biotin/avidin/biotin linkages to a derivatized surface, it will be appreciated that a wide range of different linkages, different reactive groups, different surfaces, and different orders of mixture/dilution and the like may be used to accomplish the surfaces of the invention.

In another, alternative aspect, the invention provides the relative low density of reactive moieties on a surface by steric exclusion of such reactive groups from intervening spaces. Such methods utilize other molecules or molecular components to create excluded zones upon a surface where the reactive moiety cannot be coupled. Such molecules or components may be a component of the reactive moiety or a linking molecule for the reactive moiety, or they may comprise separate molecular components. By way of example, relatively large molecules, e.g., disordered polymers, proteins, polyamino acids, large organic species, e.g., dendrons, and the like, that bear a single or a few reactive moieties may be used as spatial separators between reactive moieties that they bear (See, e.g., Hong et al., (2003) Langmuir 2357-2365.

Figure 5:
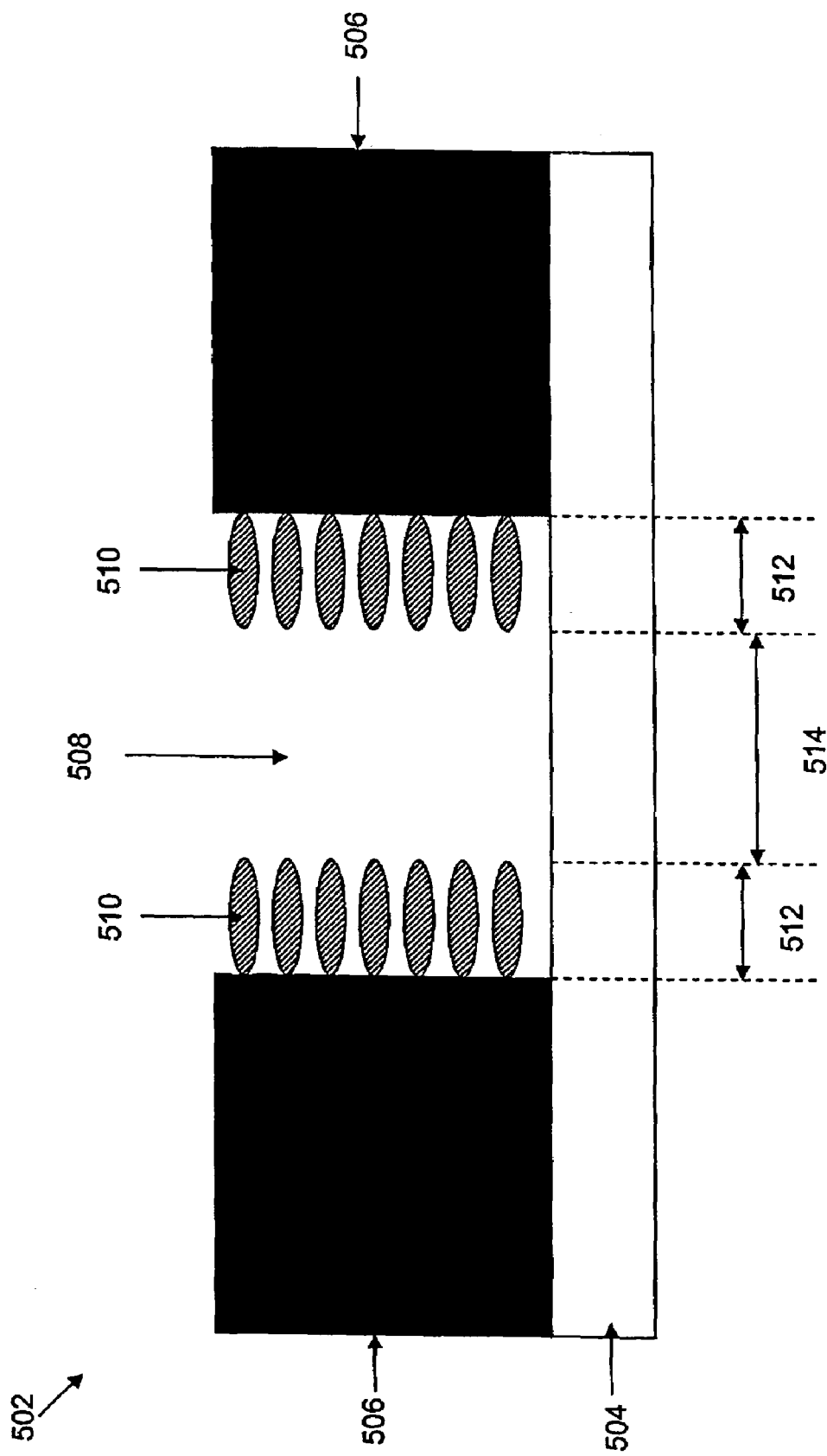
FIG. 5 schematically illustrates an example of a steric hindrance based process for producing surfaces of the invention to provide a selectively localized reactive group.

Alternatively, one class or species of surface associating molecule may be provided on a portion of a surface to exclude binding of the surface associating molecule that bears the reactive moiety within that portion. By way of example, in the case of a zero mode waveguide, or other structural confinement, one group of surface associating molecules may be selectively provided upon a wall portion of the confinement, but not on the observation area surface of the confinement. The presence of the surface associating molecules on the walls effectively reduces the cross sectional dimension of the confinement to localize any molecules coupled to the observation area nearer the center of that area. A schematic illustration of this is shown in FIG. 5. As shown, a zero mode waveguide 502 includes a base substrate 504 having a cladding layer 506 disposed thereon. The cladding layer 506 includes the wave guide core 508, constituting an aperture, disposed through it. Although such cores may vary in cross-sectional dimension, in preferred aspects, they are between about 20 nm and 200 nm in diameter. By coupling exclusion molecules 510 to the wall surfaces, one effectively reduces the radius of the substrate surface within waveguide core available for binding of reactive groups, e.g., enzymes (as indicated by dimension 514), by the effective exclusionary length of the molecules 510 on the walls (as indicated by dimensions 512). Also, because the materials used to fabricate cladding layers, e.g., layer 506, are typically a different material from the underlying substrate, e.g., metals like aluminum, gold or chrome, or silicon as opposed to silicon dioxide, one can take advantage of their different surface properties to selectively couple the exclusion molecules 510 to the wall surfaces. In the case of metal cladding materials, e.g., aluminum, chrome or gold, surface binding groups are selected that preferentially bind to the cladding surface as opposed to the underlying glass or silica based surface. For example, exclusion molecules comprising metal or metal chelating groups may be associated with the metal cladding layer, but not the underlying glass or silica based substrate. Examples of such groups include thiol groups, e.g., mercaptoundecanoic acids, in associating with thin gold layers on the cladding layer, or nitriloacetic acids, in associating with nickel layers on the cladding material, to which are coupled large molecules, e.g., polymers, disordered polymers, polyamino acids, proteins, and the like. These large molecules then shield the active groups present on the overall surface to provide a relatively low density of accessible reactive groups, or provide only sufficient space for a single catalytic reactive group, e.g., an enzyme, to localize within a given area on the observation area surface.

In yet a further alternative aspect, a low density of reactive groups of interest may be accomplished through interactions of layers within a surface structure. In particular, in some cases, the interactions of a first reactive layer coupled to the surface, with a subsequent layer may result in some subset of the subsequent layer being rendered unreactive, in the context of the reactive group of interest. In such cases, that interaction effectively operates in the same fashion as a dilution step and may be used to accomplish the goals of the invention. By way of example, a first reactive layer may include a field of biotin groups coupled to the surface through, e.g., a PEG linker. It has been observed that deposition of an avidin or streptavidin layer over the biotin layer appears to result in some level of saturation of a subset of the avidin layer. Without being bound to a particular theory of operation, it is believed that the underlying biotin linkers may be causing some measure of saturation of the avidin layer, yielding a subset of unreactive avidins, e.g., the PEG/avidin linkage may be capable of sufficient conformational flexibility to permit binding by the surface bound biotin/linker groups to multiple recognition sites on individual avidin molecules, while other avidin molecules remain unsaturated by the underlying layer. Effectively, such surfaces have resulted in a functionally diluted avidin surface, where a subset of the surface is reactive (e.g., unsaturated avidin) while the remainder of the surface is blocked (e.g., saturated avidin).

A variety of interactive sublayers may be prepared by utilizing conformationally flexible linkers, or linkers of varying lengths, e.g., a mixture of shorter and longer linkers, to engineer a sublayer that partially blocks the overlaying layer, to yield the desired density of reactive groups on the final surface.

In addition to the foregoing, it will be appreciated that while a number of methods are described that refer to the mixture of different components to create the surfaces of the invention, it many cases, it will be desirable to synthesize the desired material as a mixture, to ensure the proper ratio of each component as used. Synthesis of the ratio mixture as such, prevents surface binding variability in the constituent elements used in producing the surface, resulting from different synthesis reactions (both in terms of synthetic scheme variations, and in terms of lot to lot variability). By way of example, synthesis of mixed reactive and nonreactive groups, e.g., mixed silanes, by combining two or more precursor backbones, e.g., bearing a reactive or a non-reactive end, that are reactive with a single silane precursor, one secures uniform reactivity of the resulting silane mixture toward the surface.

with one or both of the silane group and the reactive/nonreactive groups that couple with would yield III. Exemplary Applications of Substrates and Surfaces The selectively reactive surfaces of the invention have a variety of different applications where it may be desirable to isolate individual molecules or their reactions from each other. For example, bead substrates bearing single or few reactive molecules may be readily interrogated using FACS or other bead sorting methods, to ascertain a desired reactive group in, e.g., a combinatorial chemistry library, directed evolution library, or phage display library. The surface modification techniques of the invention are applicable to such systems.

Alternatively, single molecule analyses may be performed on a given enzyme system to monitor a single reaction and effectors of that reaction. Such analyses include enzyme assays that may be diagnostically or therapeutically important, such as kinase enzymes, phosphatase enzymes, protease enzymes, nuclease enzymes, polymerase enzymes, and the like.

In preferred aspects, the surfaces are used to couple DNA polymerase enzymes at low densities in optically isolated locations on a substrate so as to analyze sequencing reactions in real-time, and monitor and identify the sequence of the synthesis reactions as they occur. Examples of a particularly preferred application of the surfaces of the invention are described in published U.S. Patent Application No. 2003/0044781, which is incorporated herein by reference in its entirety for all purposes, and particularly, the application of such methods in zero mode waveguide structures as described in U.S. Pat. No. 6,917,726, previously incorporated herein by reference in its entirety for all purposes. In particular, sequencing data from the above described sequencing methods is more easily analyzed when data from individual reactions, i.e., individual polymerase enzymes, can be isolated from data from other enzymes. By providing such enzymes on a surface at a low density, one provides physical isolation, and thus the ability to optically isolate one enzyme from another. In its most preferred aspect, a single enzyme molecule would be provided upon the observation surface of each zero mode waveguide, to permit each waveguide to provide data for a reaction of a single enzyme molecule. Because it may be difficult to assure that every wave guide or other observation area possesses a single enzyme, a density is selected whereby many waveguides will include a single enzyme, while some will include 2 or 3 or more enzymes.

As will be appreciated, the highly defined surfaces of the invention may have application across a wide spectrum of applications, technologies and industries. For example, in other applications, the surfaces of the invention may be used in any of a variety of applications where it is desirable to precisely control the level of functionality of a surface to control the physical properties of such surfaces. For example, in a number of applications, precise control of ionic groups on a surface may provide precise control of the impact of such ionic groups on the surface's interaction with its environment. By way of example, in systems used for electrophoretic and/or electroosmotic transport of materials, e.g., in microfluidic conduits, e.g., channels, capillaries, etc., precise control of the zeta potential of the surface can have broad impacts upon the electroosmotic mobility of materials within such conduits, which can, in turn, impact the relative effectiveness of the system, e.g., in electrophoretic applications.

Further, in application of high surface area conduits, e.g., capillaries or channels, one may be desirous of maintaining a certain low level of functionality at a surface while preventing excessive interactions between materials and the surface. For example, in providing dynamic coatings for capillary electrophoresis a certain level of interaction between the coating material and the surface may be desired, while little of no interaction between analytes and the surface is desired.

In still other applications, the surfaces of the invention may be used to fine tune surface modifications on medical implants and grafts, to enhance biocompatibility of such devices, by more precisely controlling the level of surface modification thereon.

One example of a modified surface according to the invention can be produced by coating the substrate surface with a mixed layer of molecules harboring reactive/attachment sites and capped or nonreactive attachement sites. In the case of silica based substrate surfaces, an exemplary mixed layer composition includes silane-PEG-X, where the X may be —OH or CH2, for a nonreactive or capped site, and carboxyl, epoxide, amine, biotin, glutathione, Ni-NTA, or other well known binding groups (see, e.g., G. T. Hermanson, Bioconjugate Techniques (Academic Press 1996). To achieve the relatively low density of reactive/attachment sites on the surface, the molar content of capped/nonreactive molecules and the molar content of reactive molecules in the applied mixture is selected to yield the desired ratio or density on the resulting surface. This ratio is determined by the binding kinetics of each component to the surface, as well as the desired end-ratio of reactive to non-reactive groups on the final surface. In addition, where a vapor deposition method is used, the relative concentration in the deposited vapor is of import, and as such, the vapor pressure of each component in the deposition chamber is factored in.

Figure 6:
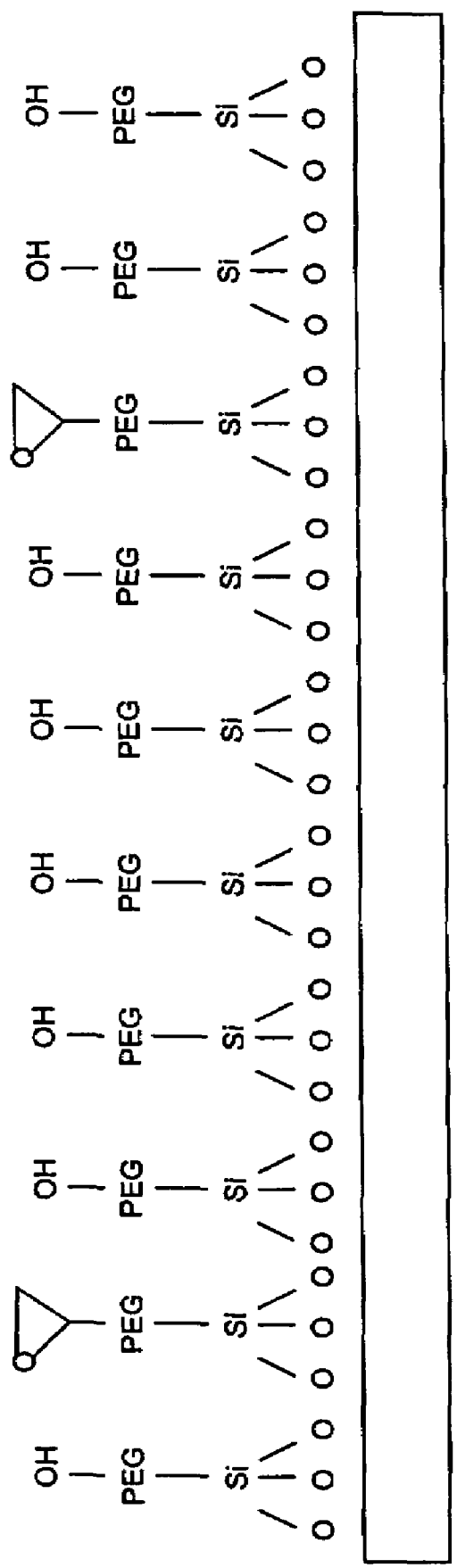
FIG. 6 is a schematic illustration of a surface having two differently functionaliozed derivatization groups disposed thereon, to yield a relatively low density reactive surface.

A schematic of the modified surface is shown in FIG. 6. As shown, a glass substrate includes an upper surface upon which silane-PEG-OH and silane-PEG-epoxide molecules are coupled, where the nonreactive silane-PEG-hydroxyl molecules far outnumber the reactive epoxide bearing groups. In related aspects, the epoxide moiety may be used to link to specific binding molecules, e.g., biotin, avidin, streptavidin, binding peptides, antibodies, antigens, glutathione, GST, which may in turn be used to couple additional molecules, e.g., catalytic molecules like enzymes, or such catalytic molecules may be directly coupled via the epoxide group. As will be appreciated, the nature of function of operation of zero mode waveguides in a variety of applications dictates that the reactive groups that are the subject of observation be relatively near the bottom surface of the waveguide. As such, a proper linkage scheme for zero mode waveguide applications will typically result in a reactive group of interest being disposed within the relevant observation volume of the waveguide, which will depend in some part upon the wavelength of light that is being used. In certain aspects, that distance is preferably between about 0 nm and about 20 nm from the bottom surface. In the case of preferred surfaces of the invention, the surface thickness that yields a desired level of reactive groups and otherwise is non-reactive will typically range from 0.8 nm to about 20 nm, and more preferably from about 1 nm to about 10 nm. Such surfaces provide sufficient rejection of interfering interactions while presenting the reactive groups within an observation volume of a preferred optical confinement.

As noted previously, the substrates of the invention are, in preferred aspects, used in conjunction with optical detection systems to monitor particular reactions occurring on these low density surfaces. In particular, these systems typically employ fluorescence detection systems that include an excitation source, an optical train for directing excitation radiation toward the surface to be interrogated, and focusing emitted light from the substrate onto a detector. One example of such a system is set forth in U.S. patent application Ser. No. 11/201,768, filed Aug. 11, 2005, and incorporated herein by reference in its entirety for all purposes.

IV. EXAMPLES

Example 1

Silane-PEG20-Biotin/Avidin Surface

A trimethoxysilane PEG20-biotin molecule was synthesized by BioLink Life Sciences (Cary, N.C.), where the "20" refers to the number of repeating ethlylene glycol units. The precursor reagents are commercially available.

The PEG20-biotin surface was fabricated by incubating substrates in 1ug PEG20-biotin per g of solvent for four hours. The solvent consisted in Methanol, 1% water by weight, and 0.1% Tween 20 non-ionic surfactant. The thickness of the PEG20-biotin coat was t=1.1 nm as measured by ellipsometry, and the water contact angle (measured within 5 seconds of drop deposition) was θ=35 degrees.

The PEG20-biotin forms a thin coating on fused silica slides and Si substrates containing a native oxide (ca 2 nm) from dilute methanol solutions (ca 1 mg PEG20-Biotin in 1 g of methanol), where the thickness varies depending upon solvent composition, and incubation time at room temperature. It was observed that when the thickness of the coating (measured by ellipsometry) reached 1 nm or more, the surfaces generally showed very good specificity towards directed binding (e.g. biotin-avidin) and high degree of rejection of protein non-specific binding. Coatings thicker than 2 nm were found not to present further improvements, while films below 0.8 nm showed less specificity towards protein binding than those 1 nm or thicker. Ellipsometric measurements carried out on Si surfaces (with native oxide) modified with PEG20-biotin showed that the thickness of the layer when coupled to Alexa488 labeled streptavidin (dry) is approximately between 3 nm and 4.3 nm thick.

A test panel was designed to demonstrate and to quantify these observations. The panel consisted of four separate areas on a fused silica slide (ca 25 mm by 75 mm). Each square is 6 mm×6 mm and was isolated from the other areas by a polydimethylsiloxane (pdms) gasket on a plastic frame window that forms a 96-well format pattern (Fast Frame® sold by Schleicher & Schuell Biosicences). Typically, each quadrant or well requires ~70 µL of solution.

The positive and negative control panels interrogated the PEG20-Biotin Surface with fluorescently labeled streptavidin (Alexa-488) or NeutrAvidin®, or labeled streptavidin or NeutrAvidin® preincubated with an excess of biotin to provide a measure of specific vs. non-specific interaction. The test panels were then interrogated with labeled φ29 polymerase to determine the level of nonspecific association of the protein (or the level of protein "rejection" provided by the surface), under different ionic strength buffer conditions, e.g., "low salts" (ca 25 mM) and "high salts (ca 150 mM).

Streptavidin (or NeutrAvidin®) binding specificity and polymerase rejection characteristics of the PEG20-biotin surfaces, were compared to the association with bare fused silica slide. All slides were rigorously cleaned with Nanostrip® followed by oxygen plasma cleaning (medium power, 5 minutes @ 2000 mTorr, Harrick xx). The protein-bound slides were scanned with a fluorescent scanning instrument. Typically the photomultiplier gain was set at 550V, and the pixel resolution was 100 µm.

The incubation conditions were as follows: A488-SA (Molecular Probes/Invitrogen) was dissolved in buffer. The A488-SA was preincubated with biotin. φ-29 polymerase was labeled with A488 using a commercial labeling kit. The enzyme was diluted in 25 mM tris, 1 mM and 5 mM β-mercaptoethanol (βME), and with added 150 mM KCl. The solutions were typically incubated for one hour. Afterwards, each well was rinsed with buffer, then water and blown-dry with an air gun.

Fused Silica and Si substrates modified with PEG20-biotin demonstrated high levels of protein "rejection" when challenged with φ-29 polymerase, which was then stained with a fluorescently labeled antibody epitope, yielding fluorescent intensities comparable to the biotin-blocked fluorescently labeled streptravidin or NeutrAvidin® in both low and high salt conditions. In particular, the results showed fluorescent intensities that were greater than 100× lower than that of the positive control (A488-SA) or protein adsorption on untreated fused silica.

A comparison of non-specific binding of φ-29 polymerase on fused silica and on PEG20-biotin surfaces showed high polymerase surface coverage (40-60%) on fused silica under low ionic strength immobilization conditions, and nearly 200 fold reduction of non-specific adsorption on PEG20-biotin (at low ionic strengths) as compared to fused silica. It also shows that PEG20-biotin presents a high degree of binding specificity towards streptavidin. The polymerase rejection characteristics of the surface decrease as the PEG layer becomes less than 1 nm thick.

Next, a panel bearing the PEG20-biotin surface was interrogated with biotinylated A488-Polymerase, mediated by non-labeled Streptavidin. Briefly, all wells on the slide bearing the PEG20-biotin surface were incubated first with streptavidin, and then interrogated with biotinylated A488-labeled polymerase that was either pre-incubated or not pre-incubated with an excess of unlabeled streptavidin, to determine the level of specific streptavidin mediated linkage to the surface. The specific interaction between the surface and the biotinylated protein showed approximately 50× increase over the non-specific interaction (where the biotinylated protein was pre-blocked with streptavidin prior to contacting it with the surface).

Example 2

Silane-PEG24-Biotin/Avidin Surface

α-biotinyl-ω-trimethoxysilyl terminated poly(ethylene glycol) (24 units) (PEG24-biotin) was synthesized by Polymer Source (Dorval, Montreal Canada).

A solution was prepared by dissolving PEG24-biotin in Ethanol at a concentration of 0.6 mg PEG24-Biotin per gram of solvent. A small amount of methanol (ca 0.4% by weight) was added to the mix to adjust the rate of deposition of the silane reagent to a Si chip (with a native oxide of ca 2 nm) between 1 nm and 1.5 nm (by ellipsometry) in three to five hours.

Fused Silica and Si substrates modified with PEG24-biotin again demonstrated low levels of non-specific interaction when challenged with fluorescently-labeled φ-29 polymerase as well as biotin-blocked Neutravidin, while at the same time showing high levels of (specific) binding towards Neutravidin and streptavidin. Restated, the surfaces of the invention have demonstrated a high level of specific interaction with desired groups, e.g., biotinylated protein, while showing low levels of non-specific binding, both of proteins, e.g., excess enzymes, as well as potentially interfering label molecules, e.g., fluorescent avidin (or by analogy, in the case of nucleic acid analyses, labeled nucleotides or nucleotide analogs, which if allowed to non-specifically adsorb within an observation area, might otherwise interfere with detection of enzymatic reactions). In this experiment, the fluorescently labeled streptavidin and polymerase were premixed with unlabeled proteins in the ratio of 1/10 in order to maintain a linear relationship between fluorescence intensity and fluorophore surface density.

Example 3

Adjusting Density of Reactive Groups

A system was prepared to test the ability to adjust the surface density of reactive functional groups using a dilution protocol. In particular, PEG24-biotin surfaces were prepared using varying dilutions of the PEG24-Biotin in a solution of N-(3-triethoxysilylpropyl)gluconamide (TES-G) is a commercial reagent (Gelest Inc, Morrisville, Pa. product #SIT8189-0).

A TES-G stock solution was prepared by dilution of 2 mg of reagent per g of a solvent mix of ethanol and 0.4% methanol. A PEG24-biotin stock solution was prepared at the concentration of 1.5 mg per gram of solvent (ethanol/methanol mix). Five aliquots of 10 mL each were prepared, and increasing amounts of PEG24-biotin stock were added to each aliquot: 0, 40 µL (0.3%), 80 µL (0.6%), 200 µL (1.4%), 400 µL (2.7%) and 800 µL (5.4%). Fused silica blanks and Si wafers were incubated simultaneously in the five aliquots for 15 h. Afterwards the substrates were removed from the reaction solutions, washed three times with methanol, annealed in air at 80 C for 10 minutes, washed in water for 10 minutes with ultrasonic agitation to remove weakly bound molecules, and dried with nitrogen gas gun. A measure of the amount of PEG24-Biotin on the surface was provided by measuring the water contact angle on the surface, where a pure PEG24surface would have a contact angle of approximately 35°.

Figure 7:
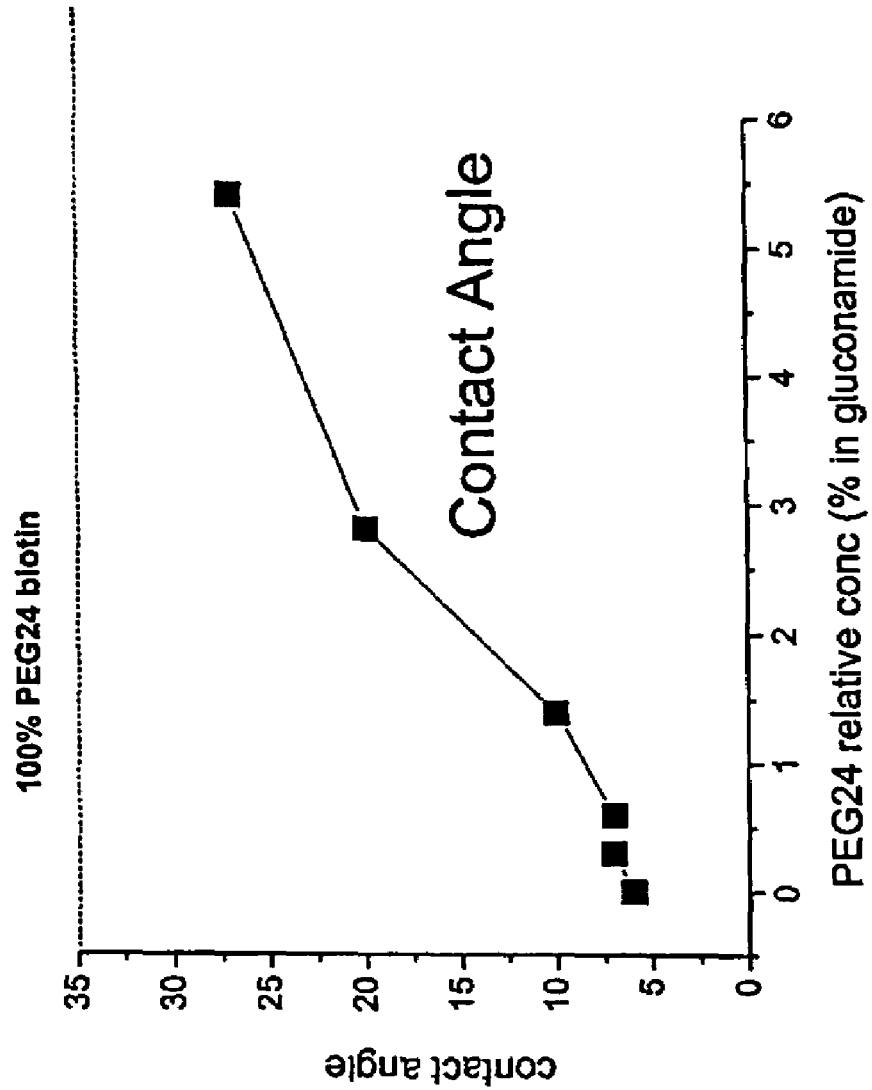
FIG. 7 is a plot of water contact angle on surfaces of varying concentrations of reactive groups among a surface of otherwise unreactive groups.

FIG. 7 shows a plot of water contact angle vs. the concentration of PEG24-biotin in TES-G, and illustrates that surface density of the active groups is readily controllable using a dilution approach.

Example 4

Mixed Functionality PEG24 Surfaces

In order to provide uniformity of surfaces, structurally similar groups were used to provide the binding or reactive group, as well as the non-reactive component of the surface. In particular, a PEG24-Biotin was diluted with a PEG24-methoxy group, similar to the PEG24 groups described in Example 2 (supra), in order to provide a surface having uniform characteristics, other than in its ability to interact with other molecules, e.g., thickness. PEG24-Methoxy was custom synthesized by Polymer Source Inc. (Dorval, Montreal, Canada) and was used as received. PEG24-methoxy was deposited on fused silica slides and Si wafers by incubating the substrates at room temperature in a solution containing 0.6 mg of reagent in ethanol with 0.4% methanol. Si substrates were removed from the solution at different time intervals to evaluate contact angle and film thickness. The rate of deposition and film thickness were comparable to PEG24-biotin films deposited under similar solvent and concentration conditions.

Silane films deposited from mixed solutions of PEG24-Methoxy and PEG24-biotin were investigated using four-quadrant panels. The PEG24-Methoxy concentration was 0.83 mg/g of ethanol/methanol solvent (0.4% methanol) and four aliquots were prepared by mixing increasing amounts of a PEG24-biotin stock solution containing 0.67 mg/g of solvent. The final solution concentrations in terms of mole percent of biotin relative to end methoxy group were 0%, 0.2%, 0.7%, and 2%. Si wafers and fused silica slides were incubated in each aliquot for 3.5 hours at room temperature. Afterwards, the substrates were rinsed three times in methanol, dried in air, annealed at 80 degrees C. for 10 minutes, and washed in water with ultrasonic mixing to remove weakly-bound PEG molecules. The thickness of the films were close to t=1.3 nm for all samples, and the corresponding contact angles were between 42° (no PEG24-biotin) to 38° (2% biotin). Binding of labeled streptavidin to the mixed surface showed good correlation with increasing molar percent of PEG24-biotin in the mixed surface, while binding of pre-blocked streptavidin was largely unchanged.

Example 5

Deposition of Low Density Reactive Polymerases on Surfaces Through Dilution of Linkage Mediating Layer The methods of the invention were used in the deposition of relatively low density of φ29 DNA polymerase enzyme in a zero-mode waveguide array, by providing a PEG24-biotin surface within each waveguide, and depositing a mixture of streptavidin and biotinylated polymerase. The ratio of Neutravidin to biotinylated polymerase was adjusted to yield a desired level of Neutravidin mediated linkage between the polymerase and the PEG-24-biotin surface, while blocking the remaining surface with excess Neutravidin.

Initially, statistical analysis was performed to determine the relative dilution of polymerase in streptavidin to yield an acceptable probability that each occupied waveguide would include no more than one polymerase enzyme. In particular, the probability of occupation ($P_{occ}$) of a Poisson statistics of average density $\mu$ is given as $P_{occ}=1-P\mu(0)=1-e(-\mu)$. For small occupation numbers $P_{occ}=\mu-\mu^2/2+\mu^3/6+O(\mu^4)$. So using Probability of occupancy as a means of measuring $\mu$ creates an error of order $\mu^2$. Therefore, one can use Probability of occupancy $P_{occ}$ as a measure of average occupation number $\mu$ whenever $\mu$ is small. For a probability of occupancy of 0.3, one can calculate the actual value of $\mu$ to be approximately 0.3567. That is, in this case. the use of the probability of occupancy as an estimate of average occupation yields an error of 16%. It is worth noting that for an average occupation number of 0.3567, there is a 70% chance that any waveguide will be empty, a 25% chance that the waveguide will contain one and exactly one polymerase and a 5% chance the waveguide will contain one or more polymerases. This illustrates that for sufficiently low occupation numbers, the use of probability of occupancy is an acceptable estimate of average occupation number.

This was then achieved by providing a dilution of biotinylated enzyme in a 50-fold excess of Neutravidin. Following dilution and deposition, the resulting waveguide arrays were tested and found to have roughly a 30% occupancy, correlating well with the probability. Further, the specific activity of the enzyme within these waveguides correlated very well to specific activity data generated on planar surfaces (which showed very high specific activity of immobilized enzyme), further validating the statistical approach.

Although described in some detail for purposes of illustration, it will be readily appreciated that a number of variations known or appreciated by those of skill in the art may be practiced within the scope of present invention. Unless otherwise clear from the context or expressly stated, any concentration values provided herein are generally given in terms of admixture values or percentages without regard to any conversion that occurs upon or following addition of the particular component of the mixture. To the extent not already expressly incorporated herein, all published references and patent documents referred to in this disclosure are incorporated herein by reference in their entirety for all purposes.

What is claimed is:

1. A substrate for monitoring enzyme activity, comprising a surface having first and second surface modifying agents coupled thereto, wherein the first surface modifying agent comprises a reactive moiety coupled thereto, and wherein the second surface modifying agent does not have the reactive moiety coupled thereto, wherein the first and second surface modifying agents are coupled to the surface by contacting the surface with a mixture of first and second surface modifying agents at a ratio of first surface modifying agent to second surface modifying agent that provides the reactive moiety coupled to the surface at a density of less than 1 reactive moiety per 100 nm$^2$, wherein the reactive moiety comprises an enzyme.

2. The substrate of claim 1 wherein the reactive moiety is coupled to the surface at a density of less than 1 reactive moiety per 1000 nm$^2$.

3. The substrate of claim 1 wherein the reactive moiety is coupled to the surface at a density of less than 1 reactive moiety per 10000 nm$^2$.

4. A substrate for monitoring enzyme activity comprising:
   a surface comprising first and second surface modifying agents coupled thereto, wherein the first surface modifying agent comprises a reactive moiety coupled thereto, and the second surface modifying agent does not comprise the reactive moiety coupled thereto; and
   wherein the first and second surface modifying agents are coupled to the surface by contacting the surface with a mixture of the first and second surface modifying agents at a ratio of the first and second surface modifying agents that provides the reactive moiety coupled to the surface at a density of between about 1 reactive moiety per 50,000 nm$^2$ and 1 reactive moiety per 100 nm$^2$, wherein the reactive moiety comprises an enzyme.

5. The substrate of claim 4, wherein the reactive moiety is coupled to the surface at a density of between about 1 reactive moiety per 8000 nm$^2$ and 1 reactive moiety per 300 nm$^2$.

6. The substrate of claim 4, wherein the reactive moiety is coupled to the surface at a density of between about 1 reactive moiety per 8000 nm$^2$ and 1 reactive moiety per 1000 nm$^2$.

7. The substrate of claim 4, wherein a remainder of the surface other than the reactive moieties is a substantially non-reactive surface.

8. The substrate of claim 4, wherein the reactive moiety is coupled to the surface through a linker group.

9. The substrate of claim 8, wherein the linker group comprises a polymer.

10. The substrate of claim 8, wherein the linker group comprises polyethylene glycol.

11. The substrate of claim 7, wherein the reactive moiety is coupled to the surface through a linker group, and the substantially non-reactive surface comprises the linker group without the reactive moiety.

12. The substrate of claim 1, wherein the enzyme is selected from a nucleic acid polymerase, a ligase, a nuclease, a protease, a kinase and a phosphatase.

13. The substrate of claim 1, wherein the enzyme comprises a DNA polymerase.

14. The substrate of claim 1, wherein the surface comprises an observation area.

15. The substrate of claim 1, wherein the surface comprises an observation surface of an optical confinement.

16. The substrate of claim 14, wherein the observation area comprises the observation surface of a zero mode waveguide.

17. The substrate of claim 1, wherein the surface of the substrate is selected from glass, quartz, fused silica, and silicon.

18. A substrate for monitoring enzyme activity, comprising:
   a surface having at least a first observation area provided therein, the observation area having an area of from about 100 nm$^2$ to 50000 nm$^2$; and
   first and second surface modifying agents coupled to the surface by contacting the surface with a mixture of the first and second surface modifying agents, wherein the first surface modifying agent comprises a reactive moiety coupled thereto, and the second surface modifying agent does not comprise the reactive moiety coupled thereto, wherein the mixture of first and second surface modifying agents comprises a ratio of first surface modifying agent to second surface modifying agent such that from 1 reactive moiety to 3 reactive moieties are coupled to the surface within the observation area, wherein the reactive moiety comprises an enzyme.

19. The substrate of claim 18, wherein the observation area is bounded by an optically opaque cladding.

20. The substrate of claim 18, wherein the enzyme comprises a DNA polymerase.

21. A method of preparing a modified surface for monitoring enzyme activity, comprising:
   providing a surface to be modified;
   contacting the surface to be modified with a surface modifying composition, wherein the surface modifying composition comprises:
      a first surface modifying agent coupled to a desired reactive moiety, and a second surface modifying agent not coupled to the desired reactive moiety; and
      the first surface modifying agent and second surface modifying agent are present in the surface modifying composition at a ratio that produces the modified surface, wherein the reactive moieties are present on the modified surface at a density of between about 1 reactive moiety per 50,000 nm$^2$ and 1 reactive moiety per 100 nm$^2$, wherein the reactive moiety comprises an enzyme.

* * * * *